United States Patent [19]

Saito et al.

[11] Patent Number: 5,239,092
[45] Date of Patent: Aug. 24, 1993

[54] PROCESS FOR PRODUCING FURYLPROPARGYLCARBINOL AND DERIVATIVE THEREOF

[75] Inventors: Kenji Saito, Hirakata; Sanshiro Matsuo; Yoshiaki Oda, both of Toyonaka, all of Japan

[73] Assignee: Sumitomo Chemical Company, Limited, Osaka, Japan

[21] Appl. No.: 974,506

[22] Filed: Nov. 12, 1992

Related U.S. Application Data

[60] Division of Ser. No. 628,101, Dec. 17, 1990, Pat. No. 5,189,186, which is a continuation-in-part of Ser. No. 543,541, Jun. 26, 1990, abandoned, which is a continuation-in-part of Ser. No. 362,107, Jun. 6, 1989, abandoned.

[30] Foreign Application Priority Data

Jun. 16, 1988 [JP] Japan ................................ 63-149829
Jul. 5, 1988 [JP] Japan ................................ 63-167922
Oct. 28, 1988 [JP] Japan ................................ 63-273910
Oct. 31, 1988 [JP] Japan ................................ 63-276849
Nov. 17, 1988 [JP] Japan ................................ 63-291906
Mar. 7, 1989 [JP] Japan ................................ 1-55784

[51] Int. Cl.$^5$ ................................................ C07D 307/02
[52] U.S. Cl. ................................................ 549/497
[58] Field of Search ........................................ 549/497

[56] References Cited

U.S. PATENT DOCUMENTS 4,352,756 10/1982 Takisawa et al. .................... 549/497
4,958,037 9/1990 Floyd, Jr. ............................ 549/497

FOREIGN PATENT DOCUMENTS 0113107 7/1984 European Pat. Off.
0247589 12/1987 European Pat. Off.
59-118780 7/1984 Japan.
63-33372 2/1988 Japan.

OTHER PUBLICATIONS

Tetrahedron Letters, vol. 26, No. 11, pp. 1449–1452 (1985).
J. Org. Chem. 1982, 47, pp. 2484–2487.
J. Org. Chem. 1984, 49, pp. 172–174.
Synthesis Communications, Jun. 1982, pp. 494–497.
Houben-Weyl: "Methoden der Organischen Chemie'-'—vol. V/2A, Georg Thieme Verlag, Stuttgart, 1977, pp. 78–104 * p. 96, Table 28; p. 99, Table 28(3).
Patent Abstracts of Japan, vol. 12, No. 242 (C-510) (3089), Jul. 8, 1988; & JP-A-63 30480 (Sumitomo Chem. Co., Ltd.) Feb. 9, 1988.
Patent Abstracts of Japan, vol. 12, No. 248 (C-511) (3095), Jul. 13, 1988; & JP-A—63 35569 (Sumitomo Chem. Co., Ltd.) Feb. 16, 1988.
Journal of Organic Chemistry, vol. 50, No. 6, Mar. 22, 1985, pp. 910–912; C. Petrier et al.: "Allylzine Reagent Additions in Aqueous Media", p. 911, Table 1.
Morrison & Boyd, *Organic Chemistry*, 3rd Edition, p. 252, 1974.
Saul Patai, "The Chemistry of Carbon-Carbon Triple Bond", pp. 381–385, 437, 755–766, 771–772, 805–812.
Organic Reactions, vol. 5 (1949).
Tetrahedron Letters, No. 51, pp. 4723–4724 (1976) (W/Translation).

*Primary Examiner*—Alan L. Rotman
*Assistant Examiner*—Raymond Covington
*Attorney, Agent, or Firm*—Stevens, Davis, Miller & Mosher

[57] ABSTRACT

A process for producing furylpropargylcarbinol or a derivative thereof represented by the formula (I):

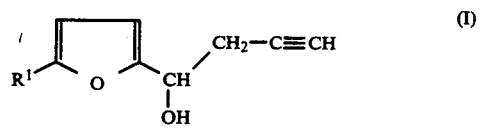

wherein $R^1$ represents hydrogen or methyl, wherein comprises subjecting a haloallylfurylcarbinol or a derivative thereof represented by the formula (II):

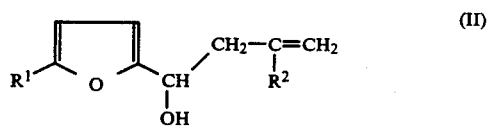

wherein $R^1$ represents a hydrogen or methyl and $R^2$ represents chlorine, bromine or iodine, to a dehydrohalogenation reaction with a base in a reaction solvent. Furylpropargylcarbinol and a derivative thereof produced according to the process of the present invention are very important as intermediates of agricultural chemicals, perfumes and medicines, and particularly applicable to intermediates of prallethrin.

9 Claims, No Drawings

PROCESS FOR PRODUCING FURYLPROPARGYLCARBINOL AND DERIVATIVE THEREOF

This is a division of application Ser. No. 07/628,101, filed Dec. 17, 1990, now U.S. Pat. No. 5,189,186 which in turn is a continuation-in-part of application Ser. No. 07/543,541, filed Jun. 26, 1990, now abandoned, which in turn is a continuation-in-part of application Ser. No. 07/362,107, filed Jun. 6, 1989, now abandoned.

BACKGROUND OF THE INVENTION

1. Field of the Industry

The present invention relates to a process for producing furylpropargylcarbinol or a derivative thereof represented by the formula (I):

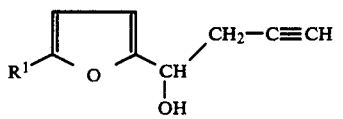
(I)

wherein $R^1$ represents a hydrogen atom or a methyl group.

The furylpropargylcarbinol and a derivative thereof are very important as intermediates of agricultural chemicals, perfumes and medicines, and particularly applicable to an intermediate of prallethrin.

2. Description of the Prior Art

As a process for producing furylpropargylcarbinol or a derivative thereof, there has heretofore been a known process using the Grignard reaction of propargyl bromide or propargyl chloride with a furfural-type compound (Japanese Patent Application Kokai No. 59-118780).

Since, however, propargyl bromide and propargyl chloride are detonable or capable of monopropellant-type burning, in view of safety, the inhibition of the detonability is required in the industrial bulk use of them. Therefore, the above-mentioned process is not always an industrially advantageous one.

SUMMARY OF THE INVENTION

The present inventors have found a process for producing furylpropargylcarbinol or a derivative thereof represented by the formula (I), using neither propargyl bromide nor propargyl chloride.

The present invention relates to a process for producing furylpropargylcarbinol or a derivative thereof represented by the formula (I) which comprises subjecting a haloallylfurylcarbinol or a derivative thereof represented by the formula (II):

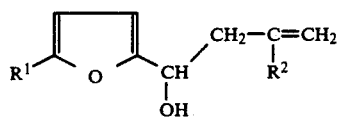
(II)

wherein $R^1$ represents a hydrogen atom or a methyl group and $R^2$ represents a chlorine atom, a bromine atom or an iodine atom, to a dehydrohalogenation reaction using a base in a solvent.

An object of the present invention is to provide a process for producing furylpropargylcarbinol and derivatives thereof being important as intermediates of agricultural chemicals, prefumes and medicines, and particularly applicable as intermediates of prallethrin.

Another object of the present invention is to provide a novel haloallylfurylcarbinol or a derivative thereof represented by the formula (II).

Further object of the invention is to provide a secure and industrially advantageous process for producing furylpropargylcarbinol and derivatives thereof or haloallylfurylcarbinols and derivatives thereof without using detonable propargyl chloride or propargyl bromide.

DESCRIPTION OF THE PREFERRED EMBODIMENTS

The base used in a dehydrohalogenation reaction according to the present invention includes alkali metal hydroxides such as sodium hydroxide, potassium hydroxide, lithium hydroxide and the like; alkali metal alkoxides such as sodium methoxide, sodium ethoxide, sodium tert-butoxide, potassium methoxide, potassium ethoxide, potassium tert-butoxide, lithium methoxide, lithium ethoxide, lithium isopropoxide and the like. Preferred examples of the alkali metal hydroxide are sodium hydroxide and potassium hydroxide. Preferred examples of the alkali metal alkoxide are sodium methoxide, sodium ethoxide, potassium methoxide, potassium ethoxide and potassium tert-butoxide.

The used amount of the base is usually 1-15 parts by mole, preferably 1-10 parts by mole for 1 part by mole of haloallylfurylcarbinol or the derivative thereof (II).

To the reaction system can be added a diamine. The diamine includes various ones, and however, are preferably aliphatic 1,2- or 1,3-diamines such as 1,2-diaminopropane, 1,3-diaminopropane, ethylenediamine, N,N,N',N'-tetramethylethylenediamine, 2,3-diaminobutane, 1,3-diaminobutane and the like; and non-aromatic 1,2- or 1,3-diamines such as 1,5-diazabicyclo[4.3.0]non-5-ene, 1,4-diazabicyclo[2.2.2]octane, 1,8-diazabicyclo[5.4.0]-undec-7-ene and the like. More preferred examples of the aliphatic 1,2- or 1,3-diamine are 1,2-diaminopropane, 1,3-diaminopropane, ethylenediamine, N,N,N',N'-tetramethylethylenediamine.

The used amount of the diamine is usually 1-20 parts by mole, preferably 1-15 parts by mole for 1 part by mole of the used haloallylfurylcarbinol or the derivative thereof (II).

The type of reaction solvent used in this reaction depends upon the type of the used base.

When the alkali metal hydroxide or alkali metal alkoxide is used as the base, there is used as the reaction solvent, alone or in admixture, a polar aprotic solvent such as acetonitrile, dimethylsulfoxide, N,N-dimethylformamide, N-methyl-2-pyrrolidinone and the like. When the diamine is liquid at room temperature, it can be also used as the reaction solvent, alone or in admixture with other diamine. Examples of the diamine are 1,2-diaminopropane, 1,3-diaminopropane, ethylenediamine, N,N,N',N'-tetramethylethylenediamine, 1,5-diazabicyclo[4.3.0]undec-7-ene and non-5-ene, 1,8-diazabicyclo[5.4.0] the like. Usually, the water content of the diamine is not more than 10% by weight, preferably not more than 5% by weight.

When the alkali metal hydroxide is used as the base, if necessary, there can be also used as the reaction solvent, water and/or an organic solvent. The organic solvent includes hydrophobic hydrocarbons such as toluene, xylene, pentane, hexane and the like; hydrophobic halogenated hydrocarbons such as monochlorobenzene, dichlorobenzene and the like; hydrophobic or hydrophilic ethers such as tetrahydrofuran, dioxane, diethyl ether, diglyme and the like. Preferably, the hydrophobic hydrocarbons are used. These organic solvents can be used alone or in admixture.

The used amount of the organic solvent is not particularly critical, and however, is usually 0.1-20 parts by weight for 1 part by weight of the used haloallylfurylcarbinol or the derivatives thereof (II). The used amount of water is 1-4 parts by weight for 1 part by weight of the used alkali metal hydroxide.

When the alkali metal hydroxide is used as the base, the reaction can be also carried out without any solvent.

Reaction temperature is usually selected in a range of 0° C.–120° C., preferably 0° C.–80° C., depending upon the combination of a base and an organic solvent.

Reaction time is not particularly critical. The end point of the reaction can be determined by following the rate of disappearance of the haloallylfurylcarbinol or the derivative thereof (II) used as a starting material.

To the reaction system, if necessary, can be added a phase transfer catalyst.

The reaction time can be shortened by the addition of a phase transfer catalyst.

The used amount thereof is usually 0.001-5 parts by mole for 1 part by mole of the used haloallylfurylcarbinol or the derivative thereof (II).

The phase transfer catalyst includes organic quaternary ammonium salts such as tetra-n-butylammonium bromide, tetra-n-butylammonium chloride, tetra-n-butylammonium hydrogen sulfate, tetra-n-pentylammonium bromide, tetra-n-pentylammonium iodide, benzyltrimethylammonium chloride, benzyltrimethylammonium bromide, benzyltriethylammonium chloride, benzyltriethylammonium bromide, benzyltripropylammonium chloride, benzyltripropylammonium iodide, cetyltrimethylammonium chloride, 1-dodecylpyridinium chloride, 1-hexadecylpyridinium chloride, 1-dodecylpyridinium bromide, 1-hexadecylpyridinium bromide and the like; organic quaternary phosphonium salts such as tetraphenylphosphonium chloride, tetraphenylphosphonium bromide, tetraphenylphosphonium iodide, benzyltriphenylphosphonium chloride and the like; macrocyclic ethers such as 18-crown-6, 15-crown-5, 12-crown-4 and the like; polyethylene glycols of various molecular weights such as polyethylene glycol 200, polyethylene glycol 300, polyethylene glycol 400, polyethylene glycol 600 and the like.

After the dehydrohalogenation reaction is completed, the furylpropargylcarbinol or the derivative thereof (I) can be obtained from the reaction mixture by, for example, the pouring of water, extraction, separation and the like followed by the distillation of an organic phase.

The haloallylfurylcarbinol or the derivative thereof (II) as a starting material of a process according to the present invention can be produced by reacting, in the presence of zinc in a solvent, furfural or a derivative thereof represented by the formula (III):

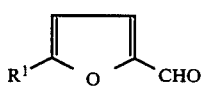

(III)

wherein $R^1$ represents a hydrogen atom or a methyl group, with an organic dihalide compound represented by the formula (IV):

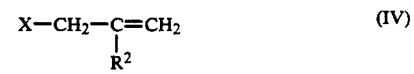

wherein each of X and $R^2$ individually represents a chlorine atom, a bromine atom or an iodine atom. Hereinafter, the reaction of furfural or a derivative thereof (III) with an organic dihalide compound (IV) is referred to as the haloallylfurylcarbinol-producing reaction.

The organic dihalide compound (IV) includes 2,3-dichloro-1-propene, 2,3-dibromo-1-propene, 2,3-diiodo-1-propene, 2-chloro-3-bromo-1-propene, 2-chloro-3-iodo-1-propene, 2-bromo-3-chloro-1-propene, 2-bromo-3-iodo-1-propene, 2-iodo-3-chloro-1-propene, 2-iodo-3-bromo-1-propene and the like.

The used amount of the organic dihalide compound (IV) is usually 1-3 parts by mole for 1 part by mole of furfural or a derivative thereof (III).

Zinc having various shapes on the market can be used. Zinc powder or zinc particles are preferably used. More preferably, zinc powder is used.

The used amount of zinc is 0.8-3 parts by mole, preferably 1.1-1.5 parts by mole for 1 part by mole of furfural or a derivative thereof (III).

There are used, if necessary, halogenated ammoniums such as ammonium chloride, ammonium bromide, ammonium iodide and the like. The used amount thereof is 0.15-6 parts by mole for 1 part by mole of furfural or a derivative thereof (III).

As the solvent of the haloallylfurylcarbinol-producing reaction, there is used water alone or a mixture of water and an organic solvent. The organic solvent includes tetrahydrofuran, dioxane, diglyme, toluene, benzene, monochlorobenzene, ethylene dichloride, polar aprotic solvents such as acetonitrile, dimethylsulfoxide, N,N-dimethylformamide, N-methyl 2-pyrrolidinone, etc., and the like.

When the solvent is a mixture, the solvent should contain water as a main component. The water content of the mixture is preferably 50% by weight or more.

The amount of water in the solvent is usually 3-24 parts by weight, preferably 4-19 parts by weight for 1 part by weight of furfural or a derivative thereof (III).

To the haloallylfurylcarbinol-producing reaction, if necessary, can be added a phase transfer catalyst. The used amount thereof is usually 0.05-0.4 parts by weight for 1 part by weight of furfural or a derivative thereof (III).

The phase transfer catalyst includes the above-mentioned organic quaternary ammonium salts.

A reaction temperature of the haloallylfurylcarbinol-producing reaction is in a range of 0° C.–100° C., preferably 15° C.–50° C.

Reaction time of the haloallylfurylcarbinol-producing reaction is usually 1-8 hours and, however, it can be shortened by the addition of a small amount of an acid.

The acid includes acetic acid, hydrochloric acid, sulfuric acid and the like.

When acetic acid is used as the acid, the added amount thereof is preferably 5% by weight or less based on the water contained in the solvent. When hydrochloric acid or sulfuric acid is used as the acid, the added amount thereof is preferably 0.1% by weight based on the water contained in the solvent.

After the haloallylfurylcarbinol-producing reaction is completed, the haloallylfurylcarbinol or the derivative thereof (II) can be obtained from the reaction mixture by, for example, filtration, separation followed by the distillation of an organic phase or by column chromatography.

Thus, according to the process of the present invention, furylpropargylcarbinol and derivatives thereof represented by the formula (I) can be produced in safety and industrially with advance.

The present invention is explained more specifically below referring to Examples and Referential Examples. However, the present invention should not be construed to be restricted by the Examples.

REFERENTIAL EXAMPLE 1

Into a reactor were charged 380 g of 30%-aqueous sodium hydroxide and 2.4 g of 68%-aqueous solution of benzyltriethylammonium chloride and the mixture was stirred at 20°–30° C. for 30 minutes. The mixture was cooled down to 10° C., and thereinto, 340 g of 30%-aqueous sodium hydroxide and 340 g of crude 1,2,3-trichloropropane having a purity of 73% were dropped together at 10°–15° C. in 25 minutes. The mixture was stirred at 10°–15° C. for 90 minutes, and thereafter, 300 g of water was added thereto. The resulting mixture was subjected to separation to obtain 248 g of an organic phase.

The content of 2,3-dichloro-1-propene in the organic phase was 71.7% by weight (yield: 95.2%), the content of 1,2,3-trichloropropane was 0.2% by weight or less.

The organic phase was subjected to simple distillation to obtain 170 g of 2,3-dichloro-1-propene having a purity of 93.8%.

EXAMPLE 1

(1) Into a reactor were charged 20.0 g of 5-methyl-furfural, 88 g of water, 33 g of toluene and 26 g of zinc powder and the mixture was kept at 33°–35° C. Thereinto, 44.4 g of distilled 2,3-dichloro-1-propene obtained in Referential Example 1 was dropped in 20 minutes. The reaction mixture was kept at 33°–35° C. for 4 hours. After the reaction was completed, the crystals derived from the zinc powder were filtered off. To the filtrate was added 66 g of toluene and a toluene phase was separated. The toluene phase was washed with 30 g of 7%-aqueous sodium carbonate and subsequently with 50 g of water, and thereafter, toluene was distilled off at 60° C. or less. The resulting residue was subjected to simple distillation to obtain 30.5 g of 2'-chloroallyl-5-methylfurylcarbinol.
Boiling point : 84°–85° C./0.8 mmHg.
Yield : 90%.
$^1$H-NMR data (measurement solvent : CDCl$_3$, internal standard : TMS, chemical shift : δ-value): 2.27 (s, 3H), 2.75–2.92 (m, 2H), 4.95 (dd, 1H), 5.25 and 5.26 (s, 2H), 5.89 (d, 1H) and 6.13 (d, 1H).

(2) The mixture of 12.3 g of 2'-chloroallyl-5-methyl-furylcarbinol obtained in (1), 42.3 g of 50%-aqueous sodium hydroxide, 37 g of toluene and 15.1 g of benzyl-triethylammonium chloride was stirred at 40° C. for 8 hours. To the mixture were added 100 g of toluene and 100 g of water, and extraction and separation were carried out. The organic phase was washed with 5%-aqueous hydrochloric acid and subsequently with 7%-aqueous sodium carbonate, and thereafter, the organic phase was concentrated under a reduced pressure.

The resulting residue was subjected to simple distillation to obtain 7.86 g of 5-methylfurylpropargylcarbinol.
Boiling point : 74° C./0.7 mmHg.
Yield : 79.2%
$^1$H-NMR data (measurement solvent : CDCl$_3$, internal standard: TMS, chemical shift: δ-value) : 2.03 (t, 1H, J=2.6 Hz), 2.25 (d, 3H, J=1.0 Hz), 2.70 (dd, 2H, J=6.6 Hz, 2.6 Hz), 2.89 (brs, 1H), 4.76 (t, 1H, J=6.6 Hz), 5.86 (dq, 1H, J=3.3 Hz, 10 Hz) and 6.17 (d, 1H, J=3.3 Hz).

EXAMPLE 2

The mixture of 12.3 g of 2'-chloroallyl-5-methylfurylcarbinol, 42.3 g of 50%-aqueous sodium hydroxide, 37 g of toluene and 21.3 g of tetra-n-butylammonium bromide was stirred at 40° C. for 8 hours. Thereafter, the same procedure was repeated as in Example 1 (2) to obtain 7.94 g of 5-methylfurylpropargylcarbinol (yield: 80.0%).

EXAMPLE 3

The mixture of 20.0 g of 2'-chloroallylfurylcarbinol, 97.4 g of 40%-aqueous potassium hydroxide, 40 g of hexane and 28.1 g of trioctylmethylammonium bromide was stirred at room temperature for 24 hours. Thereafter, the same procedure was repeated as in Example 1 (2) to obtain 13.0 g of furylpropargylcarbinol (yield: 82.3%).

EXAMPLE 4

18.66 g of 2'-chloroallyl-5-methylfurylcarbinol was dissolved in 18.66 g of toluene. To the solution was added 64.00 g of 50%-aqueous sodium hydroxide and 20.00 g of polyethylene glycol 200. The reaction mixture was kept at 40° C. for 24 hours. To the mixture, toluene and water were added, followed by extraction. The organic phase was separated, washed with 7%-aqueous sodium carbonate, and thereafter, the organic phase was concentrated under a reduced pressure. The resulting residue was subjected to simple distillation to obtain 13.35 g of 5-methylfurylpropargylcarbinol (yield 88.9%).

EXAMPLE 5

Into the mixture of 22.0 g of 5-methylfurfural, 265 g of 12.5%-aqueous ammonium chloride, 2.6 g of tetrabutylammonium bromide, 33 g of toluene and 26 g of zinc powder, 44.4 g of 2,3-dichloro-1-propene was dropped at 33°–35° C. in an hour. The reaction mixture was stirred at the same temperature for 3 hours. After the reaction was completed, the crystals derived from the zinc powder was filtered off and 66 g of toluene was added to the filtrate. A toluene phase was separated and washed with 60 g of 15%-aqueous sodium bisulfite and subsequently with 50 g of water, and thereafter, toluene was removed at 60° C. or less. The resulting concentrated residue was subjected to simple distillation to obtain 32.0 g of 2'-chloroallyl-5-methylfurylcarbinol.
Boiling point: 84°–85° C./0.8 mmHg.
Yield: 85%.

10.0 g of 2'-chloroallyl-5-methylfurylcarbinol was dissolved in 100 g of N,N-dimethylformamide. To the solution was added 6.43 g of sodium hydroxide. The reaction mixture was kept at 40° C. for 3 hours. The mixture was neutralized with 10%-aqueous hydrochloric acid, and thereafter, the solvent was distilled off under a reduced pressure. The resulting residue was added to a mixture of toluene and water. The organic phase was separated and thereafter concentrated under a reduced pressure. Thereafter, the organic phase was purified by distillation to obtain 6.92 g of 5-methylfuryl-propargylcarbinol (yield : 86.0%).

EXAMPLE 6

The mixture of 18 g of furfural, 33 g of toluene, 88 g of 3%-aqueous acetic acid and 26 g of zinc powder was kept at 33°–35° C. with stirring.

44.4 g of 2,3-dichloro-1-propene was dropped thereinto at the same temperature in 20 minutes, and thereafter, the reaction mixture was kept at the same temperature for 2 hours. After the reaction was completed the crystals derived from zinc powder was filtered off. To the filtrate was added 66 g of toluene, and the toluene phase was separated. The toluene phase was washed with 30 g of 7%-aqueous sodium carbonate and subsequently with 50 g of water. Thereafter, toluene was removed at 60° C. or less. The resulting residue was subjected to simple distillation to obtain 29.4 g of 2'-chloroallylfurylcarbinol.

Boiling point: 74° C./0.7 mmHg.
Yield 91.0%.

$^1$H-NMR data (measurement solvent : CDCl$_3$, internal standard: TMS, chemical shift: δ-value) : 2.68 (d, 1H, J=4.3 Hz), 2.83 (m, 2H), 5.00 (m, 1H), 5.24 (m, 2H), 6.25 (dd, 1H, J=3.3, 0.7 Hz), 6.32 (dd, 1H, J=3.3 , 2.0 Hz), 7.36 (dd, 1H, J=2.0, 0.7 Hz).

EXAMPLE 7

Into the mixture of 11.0 g of 5-methylfurfural, 38.4 g of 3%-aqueous acetic acid, 43.2 g of toluene and 13.1 g of zinc powder, 40.0 g of 2,3-dibromo-1-propene was dropped at 30°–35° C. in 20 minutes. After the dropping was completed, the reacting mixture was stirred at 30°–35° C. for 2 hours. After the reaction was completed, the crystals derived from the zinc powder were filtered off and the obtained crystals were washed with 86 g of toluene. The filtrate and the wash liquid were combined to obtain a filtrate mixture. The toluene phase was separated from the filtrate mixture. The toluene phase was washed with 30 g of 7%-aqueous sodium carbonate and subsequently with 50 g of water. Thereafter, toluene was removed at 60° C. or less. The resulting residue was purified by column chromatography using 100 g of silica gel as a packing and ethyl acetate as an eluent. Thereby, 11.1 g of 2'-bromoallyl-5-methylfurylcarbinol was obtained.

Yield: 48.2%.

FD-Mass spectrum data: M+ 230, M+ +2 232 .

$^1$H-NMR data (measurement solvent: CDCl$_3$ internal standard: TMS, chemical shift: δ-value): 2.08 (brs, 1H), 2.28 (d, 3H, J=1.0 Hz), 2.93 (m, 2H), 4.98 (dd, 1H, J=5.1 Hz, 8.4 Hz), 5.54 (d, 1H, J=1.7 Hz), 5.72 (d, 1H, J=1.7 Hz), 5.91 (m, 1H), 6.16 (d, 1H, J=3.3 Hz).

IR data: 3380 cm$^{-1}$ (O—H, stretching vibration), 1620 cm$^{-1}$ (vinylidene C=C, stretching vibration).

EXAMPLE 8

18.4 g of 2'-chloroallyl-5-methylfurylcarbinol was dissolved in 88.8 g of ethylenediamine. The solution was cooled to 10° C. To the solution was added 7.88 g of flaky sodium hydroxide. The reaction mixture was kept at 10° C. for 24 hours. The mixture was neutralized with acetic acid, and thereafter, undissolved cake contained in the solution were filtered off. The filtrate was concentrated under a reduced pressure. The resulting residue was subjected to simple distillation to obtain 13.66 g of 5-methylfurylpropargylcarbinol (yield 92.3%).

EXAMPLES 9–12

Reaction and post-treatment were carried out in the same manner as in Example 8, except that a haloallylfurylcarbinol or a derivative thereof, a base, a solvent shown in Table 1 were substituted for 5-methylchloroallylfurylcarbinol, sodium hydroxide and ethylenediamine. Results are shown in Table 1.

EXAMPLE 13

10.0 g of 2'-chloroallyl-5-methylfurylcarbinol was dissolved in 100 g of N-methyl-2-pyrrolidinone. To the solution was added 8.68 g of sodium methoxide. The reaction mixture was kept at 50° C. for 5 hours. The mixture was neutralized with 10%-aqueous hydrochloric acid, and thereafter the solvent was removed under a reduced pressure. The resulting residue was purified by distillation to obtain 6.10 g of 5-methylfurylpropargylcarbinol (yield : 75.8%).

TABLE 1

| Example No. | Haloallylfurylcarbinol or a derivative thereof (II) Name of compound | Amount used (g) | Base Name of compound | Amount used (g) | Solvent Name of compound | Amount used (g) | Furylpropargylcarbinol or a derivative thereof (I) Name of compound | Yield (%) |
| --- | --- | --- | --- | --- | --- | --- | --- | --- |
| 9 | 2'-chloro-allyl-5-methylfuryl-carbinol | 18.2 | KOH | 8.19 | ethylenediamine | 58.6 | 5-methyl-furyl-propargyl-carbinol | 90.2 |
| 10 | 2'-chloro-allylfuryl-carbinol | 18.0 | NaOH | 6.26 | 1,3-diamino-propane | 77.3 | furyl-propargyl-carbinol | 92.1 |
| 11 | 2'-bromo-allyl-5-methylfuryl-carbinol | 23.5 | KOH | 8.57 | 1,3-diamino-propane propane | 37.7 | 5-methyl-furyl-propargyl carbinol | 89.0 |
| 12 | 2'-chloro-allyl-5-methylfuryl-carbinol | 10.0 | NaOEt | 3.47 | ethylenediamine | 32.2 | 5-methyl-furyl-propargyl-carbinol | 92.3 |

EXAMPLE 14

Into the mixture of 9.6 g of furfural, 38.4 g of 3%-aqueous acetic acid, 43.2 g of toluene and 13.1 g of zinc powder, 40.0 g of 2,3-dibromo-1-propene was dropped at 30°-35° C. in 20 minutes. After the dropping was completed, the reaction mixture was stirred at 30°-35° C. for 2 hours. After the reaction was completed, the crystals derived from zinc powder were filtered off and the obtained crystals were washed with 86 g of toluene. The filtrate and the wash liquid were combined to obtain a filtrate mixture. The toluene phase was separated from the filtrate mixture. The toluene phase was washed with 30 g of 7%-aqueous sodium carbonate and subsequently with 50 g of water. Toluene was removed at 60° C. or less. The resulting residue was purified by column chromatography using 100 g of silica gel as a packing and ethyl acetate as an eluent. Thereby, 10.2 g of 2'-bromoallylfurylcarbinol was obtained.

Yield: 47.2%.

FD-Mass spectrum data: M+ 216, M+ +2 218.

$^1$H-NMR data (measurement solvent: CDCl$_3$, internal standard: TMS, chemical shift: δ-value): 2.28 (brs, 1H), 2.94 (m, 2H), 5.04 (dd, 1H, J=5.6, 7.9 Hz), 5.54 (d, 1H, J=1.7 Hz), 5.71 (d, 1H, J=1.7 Hz), 6.29 (m, 1H), 6.33 (m, 1H), 7.38 (m, 1H).

IR data: 3380 cm$^{-1}$ (O—H, stretching vibration), 1630 cm$^{-1}$ (vinylidene C=C, stretching vibration).

The same dehydrohalogenation reaction and post-treatment are repeated as in Example 11, except that the obtained 2-bromoallylfurylcarbinol is substituted for 2'-chloroallyl-5-methylfurylcarbinol. As a result, furylpropargylcarbinol is obtained.

EXAMPLE 15

Into the mixture of 11.0 g of 5-methylfurfural and 40.0 g of water was added each of 22.1 g of 2,3-dichloro-1-propene, 2.3 g of 50%-aqueous acetic acid and 13.1 g of zinc powder at 30°-35° C. in 3 hours. After the addition was completed, the reaction mixture was stirred at 30°-35° C. for 3 hours. After the reaction was completed, the crystals derived from the zinc powder were filtered off and the obtained crystals were washed with 120 g of toluene. The filtrate and the wash liquid were combined to obtain a filtrate mixture. The toluene phase was separated from the filtrate mixture. The toluene phase was washed with 30 g of 7%-aqueous sodium carbonate and subsequently with 50 g of water. Toluene was removed at 60° C. or less. The resulting residue was subjected to simple distillation to obtain 13.2 g of 2'-chloroallyl-5-methylfurylcarbinol (yield: 70.5%).

The same dehydrohalogenation reaction and post-treatment were repeated as in Example 1 (2), using the obtained 2'-chloroallyl-5-methylfurylcarbinol. As a result, 5-methylfurylpropargylcarbinol was obtained.

EXAMPLE 16

The mixture of 37.33 g of 2'-chloroallyl-5-methylfurylcarbinol, 56.11 g of potassium hydroxide, 112 g of toluene and 1.29 g of tetra-n-butylammonium bromide was stirred at 40° C. for 7 hours. Thereafter, the same procedure was repeated as in Example 1 (2) to obtain 24.70 g of 5-methylfurylpropargylcarbinol (yield: 82.3%).

EXAMPLE 17

The mixture of 37.33 g of 2'-chloroallyl-5-methylfurylcarbinol, 56.11 g of potassium hydroxide, and 112 g of toluene was stirred at 40° C. for 10.5 hours. Thereafter, the same procedure was repeated as in Example 1 (2) to obtain 24.42 g of 5-methylfurylpropargylcarbinol (yield: 81.3%).

EXAMPLE 18

The mixture of 37.33 g of 2'-chloroallyl-5-methylfurylcarbinol, 56.11 g of potassium hydroxide, 112 g of toluene and 1.36 g of tetra-n-butylphosphonium bromide was stirred at 40° C. for 8 hours. Thereafter, the same procedure was repeated as in Example 1 (2) to obtain 24.06 g of 5-methylfurylpropargylcarbinol (yield: 80.1%)

EXAMPLE 19

The mixture of 37.33 g of 2'-chloroallyl-5-methylfurylcarbinol, 80.00 g of sodium hydroxide, 56.0 g of toluene and 12.89 g of tetra-n-butylammonium bromide was stirred at 50° C. for 7 hours. Thereafter, the same procedure was repeated as in Example 1 (2) to obtain 22.85 g of 5-methylfurylpropargylcarbinol (yield: 76.1%).

EXAMPLE 20

The mixture of 18.67 g of 2'-chloroallyl-5-methylfurylcarbinol, 78.55 g of 50%-aqueous potassium hydroxide, and 16.98 g of tetra-n-butylammonium hydrogen sulfate was stirred at 50° C. for 7 hours. Thereafter, the same procedure was repeated as in Example 1 (2) to obtain 10.51 g of 5-methylfurylpropargylcarbinol (yield: 70.0%).

What is claimed is:

1. A haloallylfurylcarbinol or a derivative thereof represented by the formula (II):

$$\underset{R^1}{\text{[furan ring]}}\underset{O}{}\underset{\underset{OH}{|}}{CH}-CH_2-\underset{R^2}{C}=CH_2 \quad (II)$$

wherein R$^1$ represents a hydrogen atom or a methyl group and R$^2$ represents chloride, bromine or iodine.

2. A haloallylfurylcarbinol or a derivative thereof according to claim 1, wherein R$^1$ is hydrogen atom R$^2$ is chlorine.

3. A haloallylfurylcarbinol or a derivative thereof according to claim 1, wherein R$^1$ is methyl and R$^2$ is chlorine.

4. A haloallylfurylcarbinol or a derivative thereof according to claim 1, wherein R$^1$ is hydrogen and R$^2$ is bromine.

5. A haloallylfurylcarbinol or a derivative thereof according to claim 1, wherein R$^1$ is methyl and R$^2$ is bromine.

6. A process for producing a haloallylfurylcarbinol or a derivative thereof represented by the formula (II);

$$\underset{R^1}{\text{[furan ring]}}\underset{O}{}\underset{\underset{OH}{|}}{CH}-CH_2-\underset{R^2}{C}=CH_2 \quad (II)$$

wherein R$^1$ represents hydrogen or methyl and R$^2$ represents chlorine, bromine or iodine, which comprises reacting furfural or a derivative thereof represented by the formula (III):

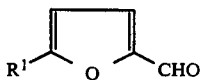 (III)

wherein R[1] represents hydrogen or methyl, with an organic dihalide compound represented by the formula (IV):

 (IV)

wherein each of R[2] and X independently represents chlorine, bromine or iodine, in the presence of zinc in a solvent selected from the group consisting of water and a mixture of water and an organic solvent.

7. A process for producing a haloallylfurylcarbinol or a derivative thereof according to claim 6, wherein the organic dihalide compound is 2,3-dichloro-1-propene or 2,3-dibromo-1-propene.

8. A process for producing a haloallylfurylcarbinol or a derivative thereof according to claim 6, wherein the reaction is carried out in the presence of an acid.

9. A process for producing a haloallylfurylcarbinol or a derivative thereof according to claim 8, wherein the organic dihalide compound is 2,3-dichloro-1-propene or 2,3-dibromo-1-propene.

* * * * *

UNITED STATES PATENT AND TRADEMARK OFFICE
CERTIFICATE OF CORRECTION

PATENT NO.  : 5,239,092
DATED       : August 24, 1993
INVENTOR(S) : Kenji SAITO et al It is certified that error appears in the above-identified patent and that said Letters Patent is hereby corrected as shown below:

ABSTRACT, line 3, "wherein" (second occurrence) should read --which--

Signed and Sealed this

Twenty-fourth Day of May, 1994

Attest:

BRUCE LEHMAN

Attesting Officer    Commissioner of Patents and Trademarks